United States Patent [19]

Weir et al.

[11] 4,234,575

[45] Nov. 18, 1980

[54] PHOSPHONOUREIDE AND PHOSPHONOTHIOUREIDE ANTHELMINTICS

[75] Inventors: W. David Weir, Levittown; Edward E. Kilbourn, Chalfont, both of Pa.

[73] Assignee: Rohm and Haas Company, Philadelphia, Pa.

[21] Appl. No.: 7,881

[22] Filed: Jan. 31, 1979

Related U.S. Application Data

[60] Division of Ser. No. 842,645, Oct. 10, 1977, Pat. No. 4,183,921, which is a division of Ser. No. 625,998, Oct. 28, 1975, Pat. No. 4,076,809, which is a continuation-in-part of Ser. No. 354,629, Apr. 25, 1973, abandoned, which is a continuation-in-part of Ser. No. 263,378, Jun. 5, 1972, abandoned.

[51] Int. Cl.³ .................. C07F 9/02; A01N 57/00; A61K 31/66
[52] U.S. Cl. .................. 424/204; 260/926; 260/938
[58] Field of Search .................. 424/204; 260/926

[56] References Cited

U.S. PATENT DOCUMENTS

| | | | |
|---|---|---|---|
| 4,076,809 | 2/1978 | Weir et al. | 424/211 |
| 4,086,336 | 4/1978 | Owen et al. | 424/204 |
| 4,120,957 | 10/1978 | Weiler et al. | 424/204 |

*Primary Examiner*—Leonard Schenkman
*Attorney, Agent, or Firm*—Jacobs & Jacobs

[57] ABSTRACT

This invention relates to novel anthelmintic compounds containing an arylene or divalent heterocyclic ring whose free valences are satisfied by
(1) a disubstituted phosphoryl ureido or thioureido group and
(2) an amino group or a substituted amido or thioamido group, to compositions containing them, and to methods of using them for the treatment of intestinal parasites in mammals and birds.

41 Claims, No Drawings

PHOSPHONOUREIDE AND PHOSPHONOTHIOUREIDE ANTHELMINTICS

This is a division of Ser. No. 842,645 filed Oct. 10, 1977 now U.S. Pat. No. 4,183,921 which is a division of Ser. No. 625,998 filed Oct. 28, 1975, now U.S. Pat. No. 4,076,809, which is a continuation-in-part of Ser. No. 354,629 filed Apr. 25, 1973, now abandoned, which in turn is a continuation-in-part of Ser. No. 263,378, filed June 5, 1972, now abandoned.

This invention relates to novel phosphorylurea compounds, to compositions containing them, and to methods of employing them to control helminths in mammals and birds.

Helminthiasis is a disease affecting man and animals and is manifested by the infection of the host with parasites known as helminths. It is a widespread disease caused by a variety of helminths found in ruminants such as sheep, cattle, and goats; equines such as horses and mules; domesticated small mammals such as dogs and cats; pigs; poultry; and man. For example, tapeworms in sheep and cattle are represented by the genera Moniezia and Thysanosma; tapeworms in horses are commonly of the genera Anoplocephala and Paranoplocephala; important tapeworms of dogs and cats include the Dipylidium and Taenia genera, as well as Echinoccocus in dogs; and poultry tapeworms include Davainea and Raillietina. In man, diphyl lobothriasis, hymenolepiasis, dipylidiasis, taeniasis, echinococcosis, and cysticerocosis, are important tapeworm infections, most of which are transmitted by animals.

Roundworms found in sheep and cattle are of the genera Strongyloides, Oesophagostomum, Bunostomum, Haemonchus, Ostertagia, Trichostrongylus, Cooperia, Nematodirus and Chabertia. Similarly, the nematode genera commonly afflicting horses are Strongylus, Strongyloides, Trichonema, Parascaris and Oxyuris. Common roundworms of dogs and cats are Toxascaris; hookworms (Ancylostoma) and whipworms (Trichuris) afflict dogs as well. Some of the intestinal nematodes of man cause trichinosis, trichuriasis, strongyloidiasis, ancylostomiasis, oxyuriasis and ascariasis. The most economically important fluke of domestic sheep and cattle is *Fasciola hepatica; this parasite bears some resemblance to the organism causing schistosomiasis in man.*

The present invention provides a new class of anthelmintic compounds capable of ridding a host animal of one or more varieties of helminths as described above, especially tapeworms and roundworms.

For convenience, these novel compounds can be represented by the following formula:

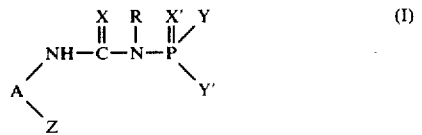
(I)

wherein

A is a divalent arylene group, such as phenylene, naphthylene, anthrylene, phenanthrylene, etc., or a divalent heterocyclic group, such as diazepinylene, pyridinylene, pyrimidylene, thienylene, furylene, etc., optionally substituted with (a) halogen, preferably chlorine;

(b) cyano;

(c) nitro;

(d) di($C_1$-$C_{18}$) alkylamino, preferably di($C_1$-$C_4$)alkylamino;

(e) vicinal alkylene of from 2 to 6 carbon atoms, preferably trimethylene;

(f) vicinal alkylenedioxy of from 1 to 4 carbon atoms, preferably methylenedioxy; or (g) a group of the formula:

$$R^1(A')_a$$

wherein $R^1$ is (1) an aliphatic group of from 1 to 18 carbon atoms;

(2) a substituted or unsubstituted aromatic group preferably containing from 6 to 10 carbon atoms in the aromatic ring;

(3) a substituted or unsubstituted heterocyclic group, preferably containing 5 or 6 members, which includes as a hetero atom, oxygen, sulfur or nitrogen, or any combination of these wherein the total number of hetero atoms does not exceed three;

(4) a substituted or unsubstituted heterocyclic-alkyl group, wherein the heterocyclic group is as described in (3) and the alkyl group preferably contains from 1 to 4 carbon atoms;

A' is oxygen, sulfur, sulfinyl, sulfonyl or carbonyl; and a is an integer of 0 to 1;

R is (a) hydrogen;

(b) ($C_1$—$C_{10}$) alkyl, preferably ($C_1$-$C_4$) alkyl;

(c) ($C_1$-$C_{10}$) haloalkyl, preferably ($C_1$-$C_4$) haloalkyl;

(d) ($C_3$-$C_6$) cycloalkyl, preferably ($C_5$-$C_6$) cycloalkyl;

(e) ($C_2$-$C_{11}$) alkoxyalkyl, preferably ($C_2$-$C_6$) alkoxyalkyl;

(f) ($C_1$-$C_{10}$) cyanoalkyl, preferably ($C_1$-$C_4$) cyanoalkyl;

(g) ($C_3$-$C_6$) alkenyl, preferably ($C_3$-$C_4$) alkenyl;

(h) ($C_3$—$C_6$) haloalkenyl, preferably ($C_3$-$C_4$) haloalkenyl;

(i) ($C_3$-$C_6$) alkynyl, preferably ($C_2$-$C_4$) alkynyl;

(j) ($C_3$-$C_6$) haloalkynyl, preferably ($C_2$-$C_4$) haloalkynyl;

(k) optionally substituted aralkyl of up to 11 carbon atoms; preferably substituted or unsubstituted benzyl; or (l) substituted or unsubstituted ($C_6$-$C_{10}$) aryl, preferably unsubstituted phenyl;

Y is R', OR', N(R')$_2$ or SR' and

Y' is OR', N(R')$_2$ or SR' wherein R' is an aliphatic group of from 1 to 18 carbon atoms, or a substituted or unsubstituted ($C_6$-$C_{10}$) aromatic group, preferably a substituted or unsubstituted phenyl group;

X is oxygen or sulfur;

X' is oxygen or sulfur, preferably oxygen; and

Z is a group of the formula:

(a) —NH$_2$, provided X is oxygen;

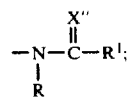
(b)

-continued

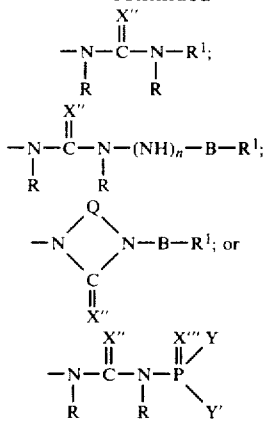

wherein R and R¹ are as defined above;
n is an integer of 0 to 1;
B is carbonyl, sulfinyl, or sulfonyl;
Q is alkylene of from 2 to 4 carbon atoms;
X" is oxygen or sulfur, provided that when X" is sulfur, X is oxygen; and
X'" is oxygen or sulfur, preferably oxygen.

A further embodiment of this invention is the metal salts and metal salt complexes of the compounds of formula I. These compounds can be represented by the following formula which is presented for illustrative purposes only:

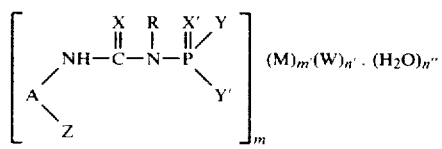

wherein
A, X, X', R, Y, Y', and Z are as defined for formula I;
M is a metal cation which can be selected from groups IA, IIA, IIIA, IB, IIB, VIIB, and VIII of the periodic table;
W is an anion such as chloride, bromide, iodide, sulfate, bisulfate, phosphate, nitrate, perchlorate, carbonate, bicarbonate, hydroxide, acetate, oxalate, malate, citrate, and the like;
m is an integer of 1–2;
m' is an integer of 1 or 2; when M is a metal cation of group IA; otherwise m' is 1;
n' is an integer of 0–1; and
n" is an integer of 0–4.

Among the compounds depicted by formula II above, the preferred compounds are those wherein the metal salt cation is a transition metal such as copper, zinc, nickel, cobalt, tin, cadmium, or manganese; an alkali metal such as sodium or potassium; or an alkaline earth metal such as calcium or magnesium, and wherein the anion is chloride, bromide, nitrate, sulfate or hydroxide. The most preferred salts are those wherein the metal salt cation is copper, zinc, nickel, cobalt, tin, cadmium, manganese, or sodium and the anion is hydroxide.

As used in the specification and claims, the terms "alkyl", "alkoxy", "alkenyl", "alkanoyl", "alkylthio", "alkylsulfinyl", "alkylsulfonyl", "dialkylamino", and the like, are intended to include straight or branched chained groups.

The term "aliphatic group" is intended to include straight or branched chain aliphatic groups such as alkyl; substituted alkyl, e.g. alkoxyalkyl, alkylthioalkyl, haloalkyl, cyanoalkyl, nitroalkyl; aralkyl; substituted aralkyl; alkenyl, substituted alkenyl, e.g. alkoxyalkenyl, alkylthioalkenyl, haloalkenyl, cyanoalkenyl, nitroalkenyl, alkenoxyalkenyl, and the like. The preferred aliphatic groups contain from 1 to 4 carbon atoms, if of the alkyl or alkenyl type; or from 7 to 10 carbon atoms, if of the aralkyl type.

Representative aliphatic groups include, for example, methyl, ethyl, sec-butyl, tert-octyl, octadecyl, ethoxyethyl, methylthiobutyl, chloroethyl, trifluoromethyl, trichloropropyl, cyanoethyl, nitrodecyl, allyl, vinyl, oleyl, stearyl, methoxyallyl, chlorovinyl, methylthiopentyl, cyanoallyl, nitrostearyl, benzyl, phenethyl, α-methylphenethyl, 3,4-dichlorobenzyl, 4-methylbenzyl, and the like.

The term "substituted", when used to modify terms such as "aromatic", "aralkyl", "phenyl", "naphthyl", "benzyl", "aryl", "heterocyclic", "heterocyclic-alkyl", and the like, is intended to refer to such groups wherein one or more, preferably one to two, hydrogen atoms on the ring are replaced by other substituents. Examples of such substituents include halogen, nitro, cyano, ($C_1$-$C_4$) alkyl, $C_1$-$C_4$(haloalkyl), ($C_1$-$C_4$) alkoxy, ($C_1$-$C_4$) alkylthio, ($C_1$-$C_4$) alkylsulfinyl, ($C_1$-$C_4$) alkylsulfonyl, ($C_1$-$C_4$) alkylcarbonyl, di($C_1$-$C_4$) alkylamino, ($C_3$-$C_4$) alkenyl, ($C_3$-$C_4$) alkenylthio, ($C_3$-$C_4$) alkenylsulfinyl, ($C_3$-$C_4$) alkenylsulfonyl, azidosulfinyl, azidosulfonyl, cyanothio, halosulfinyl, halosulfonyl, halothio, vicinal ($C_2$-$C_6$) alkylene, and the like.

The preferred substituents are halogen, preferably chlorine; nitro, ($C_1$-$C_4$) haloalkyl, ($C_1$-$C_4$) alkyl, ($C_1$-$C_4$) alkoxy, ($C_1$-$C_4$) alkylthio, ($C_1$-$C_4$) alkylsulfinyl, ($C_1$-$C_4$) alkylsulfonyl, ($C_1$-$C_4$) alkylcarbonyl, di($C_1$-$C_4$) alkylamino, ($C_3$-$C_4$) alkenylthio, ($C_3$-$C_4$) alkenylsulfinyl, ($C_3$-$C_4$) alkenylsulfonyl, azidosulfonyl, fluorosulfonyl, and vicinal trimethylene.

The preferred compounds of this invention can be represented by the following formula:

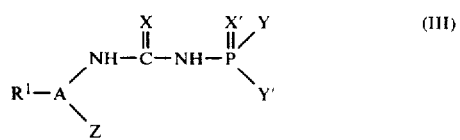

wherein
A is a divalent arylene group of the phenylene or naphthylene type;
X is oxygen or sulfur;
X' is oxygen or sulfur, preferably oxygen;
Y and Y' are independently OR', N(R')$_2$ or SR', wherein R' is ($C_1$-$C_4$) alkyl, ($C_2$-$C_4$) alkoxyalkyl, ($C_1$-$C_4$) haloalkyl, ($C_3$-$C_4$) alkenyl, phenyl, or substituted phenyl;
R¹ represents from one to four substituents when A is phenylene and from one to six substituents when A is naphthylene, which substituents can independently be
(a) ($C_1$-$C_4$) alkyl;
(b) ($C_1$-$C_4$) alkoxy;
(c) ($C_3$-$C_4$) alkenyl;
(d) halogen;

(e) nitro;
(f) a group of the formula

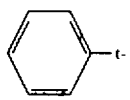

wherein t is carbonyl, sulfur, sulfinyl, or sulfonyl, provided that $R^1$ does not represent more than one

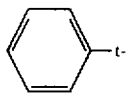

group; or (g) two $R^1$ substituents can comprise a methylenedioxy group; and

Z is a group of the formula:
(a) $NH_2$, provided X is oxygen;

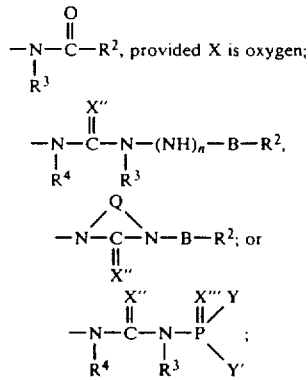

wherein $R^2$ is (a) $(C_1-C_4)$ alkyl;
(b) $(C_1-C_4)$ haloalkyl;
(b) optionally substituted aralkyl of up to 11 carbon atoms, preferably substituted or unsubstituted benzyl;
(d) substituted or unsubstituted $(C_6-C_{10})$ aryl;
(e) a substituted or unsubstituted heterocyclic group containing 5 or 6 members, which includes as a hetero atom, oxygen, sulfur, or nitrogen, preferably unsubstituted thiophene, pyridine, or furan; or
(f) a substituted or unsubstituted heterocyclic-alkyl group wherein the heterocyclic group is as described in (e) and the alkyl group preferably contains 1 to 4 carbon atoms;
$R^3$ and $R^4$ are independently (a) hydrogen,
(b) $(C_1-C_4)$ alkyl,
(c) $(C_3-C_4)$ alkenyl,
(d) $(C_2-C_4)$ alkoxyalkyl; or
(e) optionally substituted aralkyl of up to 10 carbon atoms;
B is carbonyl, sulfinyl or sulfonyl;
Q is alkylene of 2 to 4 carbon atoms; and
X" is oxygen or sulfur, provided that when X" is sulfur, X is oxygen; n is an integer of 0 to 1; and the metal salts and metal salt complexes thereof.

The most preferred compounds of this invention have a wide spectrum of anthelmintic activity and can be represented by the formula:

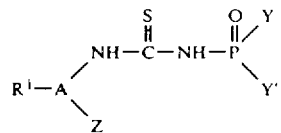

wherein
A is ortho, meta, or para phenylene, or ortho naphthylene,
Y is OR' and
Y' is OR' or SR'
wherein R' is (a) $(C_1-C_4)$ alkyl,
(b) $(C_2-C_4)$ alkoxyalkyl;
(c) allyl;
(d) $(C_1-C_4)$ haloalkyl;
(e) phenyl; or
(f) phenyl substituted with $(C_1-C_4)$ alkyl, nitro, halogen, $(C_1-C_4)$ alkoxy, $(C_1-C_4)$ haloalkyl, or di-$(C_1-C_4)$alkylamino;
$R^1$ is $(C_1-C_4)$ alkyl, $(C_1-C_4)$ alkoxy, halogen, benzoyl, benzenesulfonyl, benzenesulfinyl, or phenylthio; and represents from one to four, preferably from one to two substituents on the ring when A is phenylene, or from one to six, preferably from one to two substituents when A is naphthylene, provided that $R^1$ does not represent more than one benzoyl, benzenesulfonyl, benzenesulfinyl or phenylthio substituent; and Z is a group of the formula:

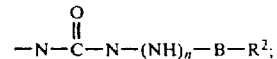

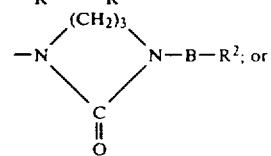

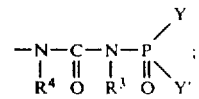

wherein $R^2$ is (a) $(C_1-C_4)$ alkyl,
(b) $(C_1-C_4)$ haloalkyl, preferably chloroalkyl;
(c) phenyl or naphthyl, preferably phenyl, optionally substituted with from one to two, preferably with one of the following substituents: $(C_1-C_4)$ alkyl, nitro, halogen, $(C_1-C_4)$ haloalkyl, di-$(C_1-C_4)$alkylamino, azidosulfonyl, $(C_1-C_4)$ alkylcarbonyl, $(C_1-C_4)$ alkylthio, $(C_1-C_4)$ alkylsulfinyl, $(C_1-C_4)$ alkylsulfonyl, or fluorosulfonyl, $R^3$ and $R^4$ are independently hydrogen, $(C_1-C_4)$ alkyl, $(C_3-C_4)$ alkenyl, $(C_2-C_4)$ alkoxyalkyl, aralkyl of up to 10 carbon atoms, preferably benzyl, which is optionally substituted with up to two halogen atoms, preferably chlorine; provided that one of $R^3$ and $R^4$ is always hydrogen;
B is carbonyl, sulfinyl, or sulfonyl; and
n is an integer of 0 to 1 and the metal salts and metal salt complexes thereof.

Among the most preferred compounds, the more preferred compounds are those wherein R' is $(C_1-C_4)$ alkyl, $(C_2-C_4)$ alkoxyalkyl, allyl or $(C_1-C_4)$ haloalkyl, B is carbonyl or sulfonyl, and $R^1$ is $(C_1-C_4)$ alkyl, $(C_1-C_4)$ alkoxy, halogen or benzoyl.

The compounds of the present invention are prepared by various methods, several of which are disclosed herein. Certain compounds of this invention can also be prepared according to the procedure disclosed in U.S. Pat. No. 3,845,176, which is hereby incorporated herein by reference. This patent discloses a multi-step process which requires only a single reaction vessel purification workup. The process disclosed comprises the following steps:

(1) reacting a thiocyanate salt and a chlorophosphate in an appropriate solvent to form the phosphonoisothiocyanate, (2) adding an o-phenylenediamine to the phosphonoisothiocyanate to form the phosphonothioureido-2-amino benzene compound, (3) adding an isocyanate or isothiocyanate to the reaction product formed in (2) to form the final product, and (4) recovering the product by physical separation, and washing with water to remove the salt formed.

It has now been found that products of higher yield and greater purity can be obtained if in the above process (a) step 1 is carried out at about 50° C., (b) step 2 is carried out at about 0° C., (c) step 3 is carried out at about 0° C., held at that temperature for about one hour, and then warmed to about 20° C. for one hour and (d) after step 4, an additional purification step is performed as described in the following paragraph.

The final product is suspended in water to which is added two equivalents of an alkali hydroxide, e.g. sodium hydroxide, to form the dialkali salt. The suspension is extracted with a solvent non-miscible in water, e.g. ether or ethyl acetate. The extract is discarded and the aqueous phase of the dialkali salt is made acidic with a mineral acid, e.g. with hydrochloric acid to a pH of from 1 to 5. The purified product precipitates and is isolated by vacuum filtration.

The following general procedures are given by way of illustration and are not to be considered as limitations of the present invention. Many variations of this invention are possible without departing from the spirit or scope hereof. The first nine sections of the general procedures deal with the preparation of starting materials necessary for compounds listed under the remaining procedure headings. All other starting materials used in the preparation of the compounds of this invention are known compounds or are readily prepared by methods available to those skilled in the art. All temperatures are in degrees Celsius.

PROCEDURE 1

Synthesis of Disubstituted Phosphoryl Isothiocyanates

The appropriate disubstituted chlorophosphate (1 mole) is added dropwise to an ice-cooled solution of potassium thiocyanate (1.1 mole) in 500 ml. of dry acetone. The suspension which forms is stirred at room temperature for two days and is concentrated in vacuo. The residue is suspended in 300 ml. benzene and washed with cold water until the washings record a pH of 5. The benzene solution is dried with magnesium sulfate and then concentrated in vacuo, giving a yellow-orange liquid. The infrared spectrum of these materials shows a strong isothiocyanate band at 4.6–5.1 microns.

Table 1 presents the results of eight such syntheses.

TABLE I $$\begin{array}{c} Y \quad O \\ \diagdown \| \\ PN{=}C{=}S \\ \diagup \\ Y' \end{array}$$

| Y | Y' | Yield |
|---|----|-------|
| $C_2H_5O-$ | $C_2H_5O-$ | 65% |
| $CH_3O-$ | $CH_3O-$ | 18.5% |
| iso-$C_3H_7O-$ | iso-$C_3H_7O-$ | 75% |
|  | | 36% |
| $(CH_3)_2N-$ | $(CH_3)_2N-$ | 41% |
| $CH_3S-$ | $C_2H_5O-$ | 45.6% |
| $C_2H_5S-$ | $C_2H_5O-$ | 24% |
| $C_3H_7S-$ | $C_2H_5O-$ | 76.4% |

PROCEDURE 2

Synthesis of Disubstituted Phosphoryl Isocyanates

An ice-cooled solution of (20 g., 0.116 mole) diethylchlorophosphate in 250 ml. ether is saturated with ammonia, yielding a white suspension that is vacuum filtered. The first crop is dried, affording a yield of 16.3 g. (0.114 mole) diethylphosphoramide, melting point 50°–51°.

To a solution of (16.3 g., 0.114 mole) diethylphosphoramide in 50 ml. 1,2-dichloroethane, oxalyl chloride (18.4 g., 0.145 mole) is added dropwise. The solution which forms is refluxed and stirred for 24 hours and is concentrated in vacuo. The residual oil is vacuum distilled, yielding 10 g. (56% yield) of pure product, boiling point 102°/15 mm.

PROCEDURE 3

Synthesis of Disubstituted Phosphorylcarbamoyl Chlorides and Thiocarbamoyl Chlorides To a solution of 16.7 g. (0.1 mole) of diethylmethylamidophosphate in 100 ml. of glyme is added 4.04 g. (0.1 mole) of 57% sodium hydride (oil dispersed). The mixture is stirred at room temperature for three hours and is added dropwise to an ice-cooled solution of 12.5% phosgene (99 g., 0.125 mole) in benzene. The resultant suspension is stirred at room temperature overnight and is vacuum filtered through celite. The filtrate is concentrated in vacuo to afford 14.3 g. of product as a yellow oil. The thiocarbamoyl chlorides are prepared in an analagous manner by using thiophosgene.

PROCEDURE 4

Synthesis of Aryl or Alkylsulfonylisothiocyanates

To a solution of the aryl or alkylsulfonamide (1 mole) and carbon disulfide (1 mole) in 50 ml. dry dimethylformamide, potassium hydroxide is added as pellets. The suspension which forms is stirred at room temperature for two hours, after which more potassium hydroxide (1 mole) is added. The temperature of the exothermic reaction is kept at 35° with ice cooling. A thick suspension forms which is stirred for 24 hours at room temperature and then vacuum filtered. Table 2 presents the results of two such syntheses.

To the dipotassium salt (0.48 mole), phosgene (0.5 mole in a 12.5% benzene solution) is added with ice cooling and stirring. The resultant suspension is stirred at room temperature for 24 hours under anhydrous conditions and then filtered. The potassium chloride residue is washed with ether (3×100 ml.), and the filtrate and washings are concentrated in vacuo. The yellow-orange oil obtained is of high purity. The infrared spectrum shows an isothiocyanate band at 4.9–5.4 microns. Table 3 presents the results of two such synthesis.

TABLE 2

| Dipotassium Alkyl or Arylsulfonyl Iminoisothiocyanates | R | Yield | Melting Point (°C.) |
|---|---|---|---|
| R—SO$_2$N=C(SK)(SK) | CH$_3$— | 95% | 281 (decomposed) |
|  | CH$_3$CH$_2$— | 80% | 225°–229° (decomposed) |
|  | CH$_3$—⟨phenyl⟩— | 70% | 242°–248° (decomposed) |

TABLE 3

| Alkyl or Aryl Sulfonylisothiocyanates | R | Yeild |
|---|---|---|
| R—SO$_2$N=C=S | CH$_3$— | 95% |
|  | CH$_3$CH$_2$— | 91% |
|  | CH$_3$—⟨phenyl⟩— | 89% |

The aralkyl, heterocyclic, and heterocyclic-alkyl sulfonylisothiocyanates can be prepared in an analogous manner.

PROCEDURE 5

Synthesis of Arylsulfonylisocyanates

Oxalyl chloride (16.5 g., 0.13 mole) is added in one portion to an ice cooled suspension of the arylsulfonamide (0.1 mole) in 100 ml. of anhydrous chlorobenzene. The mixture is allowed to warm to room temperature and is then refluxed and stirred for 24 hours. The suspension is cooled and vacuum filtered through diatomaceous earth. The filtrate is stripped of its solvent content in vacuo, and the residue is vacuum distilled to yield the product. The product is identified by the infrared band at 4.5 microns, characteristic of isocyanate.

Table 4 presents the results of four such syntheses.

TABLE 4

| Arylsulfonylisocyanate | R | Yield | Boiling Point |
|---|---|---|---|
| R—SO$_2$N=C=O | ⟨phenyl⟩— | 25% See Note 1 | 101°/1.75mm |
|  | O$_2$N—⟨phenyl⟩— | 5.25% | 131°–135°/0.7mm |
|  | (CH$_3$)$_2$N—⟨phenyl⟩— | 85% | See Note 2 |
|  | ⟨indanyl⟩ | 18.4% | 130°–135°/0.7mm |

Note 1
Reaction was initiated in ethylene dichloride; solvent was then changed to chlorobenzene to effect thermal decomposition of the intermediate at about 148°.
Note 2
Reaction performed with 0.0475 moles of the sulfonamide and 0.06 moles of oxalyl chloride. Product decomposes rapidly at high temperature.

The aralkyl, heterocyclic, and heterocyclic-alkyl sulfonylisocyanates can be prepared in a manner analogous to that of procedure five. The alkylsulfonylisocyanates can be prepared in accordance with U.S. Pat. No. 3,185,677.

PROCEDURE 6

Preparation of Arylsulfonylcarbamoyl Chlorides or Thiocarbamoyl Chlorides

To a solution of the appropriate sulfonamide in an aprotic solvent, e.g. glyme, is added an equimolar amount of sodium hydride (oil dispension) with stirring at room temperature. To the resultant suspension, which is cooled in an ice bath, is added with stirring, a solution of a molar excess of phosgene in benzene. The suspension is stirred overnight, the precipitate is filtered and the filtrate is concentrated in vacuo to yield the product. The thiocarbamoyl chlorides are prepared in an analogous manner using thiophosgene. Table 5 presents the results of two such syntheses.

TABLE 5

| Arylsulfonylcarbamoyl chloride | R | X | Yield |
|---|---|---|---|
| R—SO$_2$N(X)C(O)—Cl (a) | H$_3$C—⟨phenyl⟩— | —CH$_3$ | 100% |
| (b) | H$_3$C—⟨phenyl⟩— | —CH$_2$—⟨phenyl⟩ | 74% |

|  | Sulfonamide (Mole) | Sodium hydride (Mole) | Phosgene (Mole) | Solvent |
|---|---|---|---|---|
| (a) | 0.5 | 0.5 | 0.08 | glyme |
| (b) | 0.05 | 0.05 | 0.06 | glyme |

The alkyl, aralkyl, heterocyclic and heterocyclic-alkyl sulfonylcarbamoyl and thiocarbamoyl chlorides can be prepared in a manner analogous to that of procedure six.

PROCEDURE 7

Synthesis of Alkanoyl or Aroylisothiocyanates

The appropriate alkanoyl or aroyl chloride (0.25 mole) is added to a benzene suspension of lead thiocyanate (97 g., 0.3 mole), and the mixture is refluxed and stirred for 24 hours and then vacuum filtered through diatomaceous earth. The filtrate is concentrated in vacuo and is vacuum distilled. The infrared spectrum of these materials shows strong isothiocyanate bands at 4.8–5.2 microns and $$\begin{matrix} O \\ \| \\ R-C- \end{matrix}$$

bands at 5.8–5.9 microns.

Table 6 presents the results of six such syntheses.

TABLE 6

| Alkanoyl or Aroylisothiocyanates | R |  |  |
|---|---|---|---|
| RCN=C=S (O) | CH$_3$— | 40% | 57°/32mm |
|  | CH$_3$CH$_2$— | 54% | 81°/60mm |
|  | ClCH$_2$— | 35% | 98°/50mm |
|  |  | 40% | 90°/1.3mm |

TABLE 6-continued

| Alkanoyl or Aroylisothiocyanates | R | | |
|---|---|---|---|
| | CH₃—⟨phenyl⟩— | 60% | 88°/0.4mm |
| | CCl₃—⟨phenyl⟩— | 60% | 125°/0.2mm (also melting point: 61°–65°) |

PROCEDURE 8

Synthesis of Alkanoyl or Aroylisocyanates

To a solution of the appropriate amide in ethylene dichloride, oxalyl chloride is added dropwise. The solution which forms is refluxed and stirred for 24 hours and is then concentrated in vacuo. The residual oil is vacuum distilled.

Table 7 presents the results of two such syntheses.

TABLE 7

| Aroylisocyanate | R | Yield | Boiling Point |
|---|---|---|---|
| $$R-\overset{O}{\underset{\|}{C}}-N=C=O$$ | (a) CH₃—⟨phenyl⟩— | 52.5% | 94–95°/4.5mm |
| | (b) O₂N—⟨phenyl⟩— | 86% | See Note 3 |
| Amide | Oxalylchloride | | |

TABLE 7-continued

| | (mole) | (mole) | Solvent |
|---|---|---|---|
| (a) | 0.1 | 0.12 | 200ml |
| (b) | 0.1 | 0.13 | 350ml |

Note 3
Solid showed slight decomposition at 90°; decomposition product remained solid to 225°. Another sample showed a total decomposition when placed in preheated 130° bath.

The aralkanoyl, heterocyclic-carbonyl, and heterocyclic-alkylcarbonyl isothiocyanates and isocyanates can be prepared in a manner analogous to procedures 7 and 8 respectively.

PROCEDURE 9

Synthesis of 1-(3-Disubstituted Phosphorylthioureido)-2-Aminobenzene Compounds To a solution of the desired ortho arylene diamine or ortho heterocyclic diamine in an aprotic solent is added one equivalent of the desired phosphoryl isothiocyanate (exothermic reaction). The reaction mixture is maintained at room temperature for the reaction period indicated in Table 8, and a precipitate is formed. The product isolated by vacuum filtration and is identified by elemental analysis and infrared spectrum. Table 8 presents the results of sixteen such syntheses.

The compounds listed in Table 8 are disclosed and claimed in application Ser. No. 259,423, entitled "Phosphorylthioureide Anthelmintics," filed May 26, 1972, by Schneider et al., and assigned to a common assignee.

TABLE 8

$$A\begin{cases} NH-\overset{O}{\underset{\|}{C}}-NH-\overset{O}{\underset{\|}{P}}\diagdown\overset{Y}{\underset{Y'}{}} \\ NH-R^{1} \end{cases}$$

| | R¹ | Y | Y' | Melting Point |
|---|---|---|---|---|
| 1 | ⟨o-tolyl⟩ | H | —OC₂H₅ | —OC₂H₅ | 135–138° dec. |
| 2 | ⟨o-tolyl⟩ | H | —OC₃H₇-iso | —OC₃H₇iso | 116–117.5° dec. |
| 3 | ⟨dimethylphenyl-C(O)-phenyl⟩ | H | —OC₂H₅ | —OC₂H₅ | 155° dec. |
| 4 | ⟨o-tolyl⟩ | —CH₃ | —OC₂H₅ | —OC₂H₅ | 110–114° dec. |
| 5 | ⟨o-tolyl⟩ | —C₄H₉ | —OC₂H₅ | —OC₂H₅ | 78–80° dec. |
| 6 | ⟨o-tolyl⟩ | —CH₂CH=CH₂ | —OC₂H₅ | —OC₂H₅ | 69–72° dec. |
| 7 | ⟨o-tolyl⟩ | —CH₂—⟨phenyl⟩ | —OC₂H₅ | —OC₂H₅ | 115–118° dec. |
| 8 | ⟨o-tolyl⟩ | —(CH₂)₃OCH₃ | —OC₂H₅ | —OC₂H₅ | 76–79° dec. |
| 9 | ⟨o-tolyl⟩ | H | OC₂H₅ | SC₂H₅ | 121–124° slight dec. |
| 10 | ⟨o-tolyl⟩ | H | —OC₂H₅ | —SCH₃ | 131–133° dec. |
| 11 | ⟨o-tolyl⟩ | H | —OC₂H₅ | —SC₃H₇ | 85–93° |

TABLE 8-continued $$\begin{array}{c} \text{NH}-\overset{\overset{\displaystyle O}{\|}}{\text{C}}-\text{NH}-\overset{\overset{\displaystyle O}{\|}}{\text{P}}\diagdown\!\!\diagup\!\!\!Y \\ A\diagup\qquad\qquad\qquad Y' \\ \diagdown\text{NH}-R^1 \end{array}$$

| No. | (structure) | A | (R group) | (Y) | (Y') | m.p. |
|---|---|---|---|---|---|---|
| 12 | (phenyl) | H | —N(CH₃)₂ | —N(CH₃)₂ | | 136–137° |
| 13 | (phenyl) | H | —O(CH₂)₂Cl | —O(CH₂)₂Cl | | 111–120° |
| 14 | (naphthyl) | H | —OC₂H₅ | —OC₂H₅ | | 148–151° dec. |
| 15 | (phenanthryl) | H | —OC₂H₅ | —OC₂H₅ | | 175–177° dec. |
| 16 | (pyridyl) | H | —OC₂H₅ | —OC₂H₅ | | 133–136.5° decc. |

| No. | Diamine (Mole) | Isothiocyanate (Mole) | Reaction Solvent | Reaction Time | Precipitating Solvent |
|---|---|---|---|---|---|
| 1 | 0.186 | 0.186 | glyme | 18 hrs. | none |
| 2 | 0.186 | 0.186 | glyme | 18 hrs. | ether |
| 3 | 0.03 | 0.03 | acetone | 2 hrs. | none |
| 4 | 0.02 | 0.02 | glyme | 24 hrs. | water |
| 5 | 0.02 | 0.02 | glyme | 6 days | water |
| 6 | 0.01 | 0.01 | glyme | 1 week | water |
| 7 | 0.02 | 0.02 | glyme | 2 hrs. | none |
| 8 | 0.0205 | 0.0205 | ethyl acetate | 2 hrs. | hexane |
| 9 | 0.0118 | 0.0118 | glyme | 24 hrs. | water |
| 10 | 0.01 | 0.01 | glyme | 18 hrs. | water |
| 11 | 0.01 | 0.01 | glyme | 18 hrs. | water |
| 12 | 0.02 | 0.02 | glyme | 3 hrs. | none |
| 13 | 0.076 | 0.076 | glyme | 2 hrs. | none |
| 14 | 0.01 | 0.01 | glyme | 18 hrs. | none |
| 15 | 0.005 | 0.005 | glyme | 4 days | none |
| 16 | 0.01 | 0.01 | glyme | 15 min. | none |

PROCEDURE 10

Synthesis of 1-(3-Disubstituted Phosphorylureido)-2-Aminobenzene Compounds

To a solution of 6.03 g. (0.5575 mole) of an ice-cooled solution of o-phenylene diamine in 25 ml. of glyme is added 10 g. (0.5575 mole) of diethylphosphonoisocyanate. The resultant suspension is stirred at room temperature for 2–3 days and then vacuum filtered to afford a first crop yield of 12.5 g. (76%) m.p. 137–140, slight decomposition.

PROCEDURE 11

Synthesis of 1-(3-Disubstituted Phosphorylthioureido)-2-(3-Substituted Sulfonyl or Carbonylureido, or 3-Disubstituted Phosphorylureido) Benzene Compounds and Analogous Compounds To a mixture in glyme or other solvent of the appropriate 1-(3-disubstituted phosphorylureido or thioureido)-2-aminobenzene compound is added the appropriate isocyanate (exothermic reaction). The reaction mixture is maintained at room temperature for the reaction period indicated in Table 9, and a precipitate forms. The product is isolated by vacuum filtration and is identified by elemental analysis and infrared spectrum. Thirty-two compounds prepared in a manner analogous to that of procedure 11 are presented in Table 9.

TABLE 9

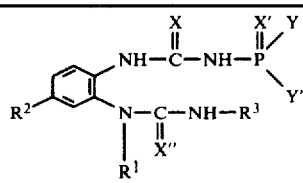

Melting

TABLE 9-continued

| No. | R¹ | R² | R³ | X | X' | X'' | Y | Y' | Point |
|---|---|---|---|---|---|---|---|---|---|
| 1 | H | H | —SO₂—C₆H₅ | S | O | O | —OC₂H₅ | —OC₂H₅ | 174°–175° dec. |
| 2 | H | H | —SO₂—C₆H₄—CH₃ | S | O | O | —OC₂H₅ | —OC₂H₅ | 162°–164° dec. |
| 2' | H | H | —SO₂—C₆H₄—CH₃ | S | O | O | —OC₂H₅ | —OC₂H₅ | 168°–169° dec. |
| 3 | H | Cl | —SO₂—C₆H₄—CH₃ | S | O | O | —OC₂H₅ | —OC₂H₅ | 96°–106° dec. |
| 4 | H | H | —SO₂—C₆H₄—Cl | S | O | O | —OC₂H₅ | —OC₂H₅ | 162°–165° dec. |
| 5 | H | H | —SO₂-indanyl | S | O | O | —OC₂H₅ | —OC₂H₅ | 167°–169° dec. |
| 6 | H | —C(=O)—C₆H₅ | —SO₂—C₆H₄—CH₃ | S | O | O | —OC₂H₅ | —OC₂H₅ | 104°–108° slow dec. |
| 7 | —CH₃ | H | —SO₂—C₆H₄—CH₃ | S | O | O | —OC₂H₅ | —OC₂H₅ | 150°–152° dec. |
| 8 | —C₄H₉ | H | —SO₂—C₆H₄—CH₃ | S | O | O | —OC₂H₅ | —OC₂H₅ | 151.5°–153° dec. |
| 9 | —CH₂CH=CH₂ | H | —SO₂—C₆H₄—CH₃ | S | O | O | —OC₂H₅ | —OC₂H₅ | 149°–151° dec. |
| 10 | —CH₂—C₆H₅ | H | —SO₂—C₆H₄—CH₃ | S | O | O | —OC₂H₅ | —OC₂H₅ | 116°–118.5° dec. |
| 11 | —(CH₂)₃OCH₃ | H | —SO₂—C₆H₄—CH₃ | S | O | O | —OC₂H₅ | —OC₂H₅ | 114°–119° dec. |
| 12 | H | H | —SO₂—C₆H₄—CH₃ | S | O | O | —OC₂H₅ | —SC₂H₅ | 157°–160° dec. |
| 13 | H | H | —SO₂—C₆H₄—CH₃ | S | O | O | —OC₂H₅ | —SCH₃ | 157.5°–159° dec. |
| 14 | H | H | —SO₂—C₆H₄—CH₃ | S | O | O | —OC₂H₅ | —SC₃H₇ | 144°–146° dec. |
| 15 | H | H | —SO₂—C₆H₄—CH₃ | S | O | O | —N(CH₃)₂ | —N(CH₃)₂ | 146°–148° dec. |
| 16 | H | H | —SO₂—C₆H₄—CH₃ | S | O | O | —O(CH₂)₂Cl | —O(CH₂)₂Cl | 150°–153° dec. |
| 17 | H | H | —SO₂—C₆H₄—CH₃ | S | O | O | —OC₃H₇-iso | —OC₃H₇-iso | 145°–147° dec. |
| 18 | —CH₂—C₆H₃Cl₂ | H | —SO₂—C₆H₄—CH₃ | S | O | O | —OC₂H₅ | —OC₂H₅ | 72°–100° dec. |
| 19 | H | H | naphthyl-SO₂— | S | O | O | —OC₂H₅ | —OC₂H₅ | 167°–168° dec. |
| 20 | H | H | —SO₂—C₆H₄—CH₃ | O | O | O | —OC₂H₅ | —OC₂H₅ | 136°–140° dec. |
| 21 | H | H | —SO₂CH₃ | O | O | S | —OC₂H₅ | —OC₂H₅ | 169°–171° dec. |
| 22 | H | H | —SO₂C₂H₅ | O | O | S | OC₂H₅ | OC₂H₅ | 169°–170° dec. |
| 23 | H | H | —C(=O)—C₆H₄—CH₃ | S | O | O | —OC₂H₅ | —OC₂H₅ | 235°–240° dec. |
| 24 | H | H | —C(=O)—C₆H₄—NO₂ | S | O | O | —OC₂H₅ | —OC₂H₅ | 240°–242° dec. |
| 25 | H | H | —C(=O)—CH₃ | O | O | S | OC₂H₅ | OC₂H₅ | 169°–171° dec. |
| 26 | H | H | —C(=O)—C₂H₅ | O | O | S | OC₂H₅ | OC₂H₅ | 183.5°–185° dec. |

TABLE 9-continued

| No. | R¹ | R² | R³ | X | X' | X" | Y | Y' | Melting Point |
|---|---|---|---|---|---|---|---|---|---|
| 27 | H | H | $-\overset{O}{\underset{\|}{P}}(OC_2H_5)_2$ | O | O | O | $-OC_2H_5$ | $-OC_2H_5$ | 152°–154° dec. |
| 28 | H | H | $-\overset{O}{\underset{\|}{P}}(OC_2H_5)_2$ | S | O | O | $-OC_2H_5$ | $-OC_2H_5$ | 139°–143.5° dec. |
| 29 | H | H | $-\overset{O}{\underset{\|}{P}}(OC_2H_5)_2$ | S | S | O | $-OC_2H_5$ | $-OC_2H_5$ | 80°–82° |
| 30 | H | H | $-\overset{O}{\underset{\|}{P}}\overset{SC_3H_7\text{-}iso}{\underset{OC_2H_5}{}}$ | S | O | O | $-OC_2H_5$ | $-OC_2H_5$ | 89°–91° dec. |
| 31 | H | H | $-\overset{O}{\underset{\|}{P}}\overset{SC_3H_7\text{-}iso}{\underset{OC_2H_5}{}}$ | O | O | S | $-OC_2H_5$ | $-OC_2H_5$ | 85°–87° dec. |

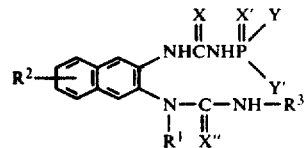

| No. | R¹ | R² | R³ | X | X' | X" | Y | Y' | Melting Point |
|---|---|---|---|---|---|---|---|---|---|
| 32 | H | H | $-SO_2-\text{C}_6\text{H}_4-CH_3$ | S | O | O | $-OC_2H_5$ | $-OC_2H_5$ | 175°–178.5° dec. |

| No. | Aminobenzene Compound (Mole) | Acylating Agent (Mole) | Reaction Solvent | Reaction Time | Precipitating Solvent |
|---|---|---|---|---|---|
| 1 | 0.0123 | 0.0123 | glyme | 24 hrs. | none |
| 2 | 0.00595 | 0.00595 | benzene | 2½ hrs. | none |
| *2' | 1.0 | 1.0 | glyme | 1 hr. | none |
| 3 | 0.1 | 0.1 | glyme | 4 days | water |
| 4 | 0.02 | 0.02 | glyme | 15 min. | none |
| 5 | 0.0092 | 0.0092 | glyme | 24 hrs. | none |
| 6 | 0.001 | 0.001 | glyme | 18 hrs. | water |
| 7 | 0.00252 | 0.00252 | ethyl acetate | 5 min. | none |
| 8 | 0.005 | 0.005 | glyme | 18 hrs. | ether |
| 9 | 0.003 | 0.003 | glyme | 24 hrs. | ether |
| 10 | 0.0076 | 0.0076 | glyme | 1 hr. | none |
| 11 | 0.00534 | 0.00534 | ethyl acetate | 24 hrs. | hexane |
| 12 | 0.00313 | 0.00313 | glyme | 2 hrs. | none |
| 13 | 0.00328 | 0.00328 | glyme | 2 hrs. | none |
| 14 | 0.002 | 0.002 | glyme | 18 hrs. | ether |
| 15 | 0.00333 | 0.00333 | glyme | 2 hrs. | none |
| 16 | 0.005 | 0.005 | glyme | 2 hrs. | none |
| 17 | 0.01 | 0.01 | glyme | 5 days | water/ether |
| 18 | 0.00065 | 0.00065 | glyme | 1 week | water |
| 19 | 0.00774 | 0.00774 | glyme | 18 hrs. | none |
| 20 | 0.00523 | 0.00523 | glyme | 30 min. | none |
| 21 | 0.01 | 0.03 | glyme | 30 min. | none |
| 22 | 0.01 | 0.02 | glyme | 30 min. | none |
| 23 | 0.01 | 0.01 | glyme | 10 min. | none |
| 24 | 0.01 | 0.01 | acetonitrile | 30 min. | none |
| 25 | 0.01 | 0.025 | glyme | 30 min. | none |
| 26 | 0.01 | 0.03 | glyme | 18 hrs. | none |
| 27 | 0.01 | 0.01 | glyme | 3 days | none |
| 28 | 0.01 | 0.01 | glyme | 7 days | none |
| 29 | 0.02 | 0.02 | acetonitrile | 1½ hrs. | ether/hexane |
| 30 | 0.01 | 0.01 | ethyl acetate | 18 hrs. | ether/hexane |
| 31 | 0.009 | 0.009 | ethyl acetate | 3 hrs. | ether/hexane |
| 32 | 0.00283 | 0.00283 | glyme | 18 hrs. | none |

*Reaction conducted at reflux

PROCEDURE 12

Synthesis of 1-(3-Disubstituted Phosphorylureido or Thioureido)-2-Substituted Amidobenzene Compounds (A) To a suspension of a 1-(3-disubstituted phosphorylthioureido or ureido)-2-aminobenzene compound suspended in an aprotic solvent is added the appropriate acylating agent indicated in Table 10 (isocyanate, acid halide, or carbamoyl chloride). The reaction mixture is maintained at room temperature for the reaction period indicated in the Table, and a precipitate is formed. The product is isolated by vacuum filtration and is identified by elemental analysis and infrared spectrum. Compounds 1 to 11 in Table 10 were prepared in accordance with this procedure.

(B) To a suspension of the desired monoacylated arylene diamine in an aprotic solvent is added the appropriate phosphorylisothiocyanate or isocyanate. In some cases, it may be necessary to briefly heat the reaction mixutre to initiate the reaction; however, initial heating is probably not required to prepare any of the compounds in Table 10. The reaction mixture is maintained at room temperature for the indicated period and a precipitate forms. The product is isolated by vacuum filtration and is identified by elemental analysis and infrared spectrum. Compounds 12 to 18 in Table 10 were prepared in accordance with this procedure.

TABLE 10

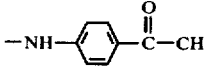

| No. | X | R | Melting Point |
|---|---|---|---|
| 1 | S | —NH—C₆H₄—C(O)—CH₃ | 137°–141° dec. |
| 2 | O | —C₆H₄—SO₂F | 198°–201° dec. |
| 3 | S | —NHNHSO₂—C₆H₄—CH₃ | 157°–159° dec. |
| 4 | O | —NHCH₂CH₂Cl | 159°–162° dec. |
| 5 | S | —NH—C₆H₄—NO₂ | 154°–155° dec. |
| 6 | S | —NH—C₆H₄—SO₂F | 170°–173° dec. |
| 7 | S | —NH—C₆H₄—SCH₂CH=CH₂ | 140°–142° dec. |
| 8 | S | —NH—C₆H₄—SCH₃ | 124°–127° dec. |
| 9 | S | —N(CH₃)—SO₂—C₆H₄—CH₃ | 140°–143° dec. |
| 10 | S | —N(CH₂C₆H₅)—SO₂—C₆H₄—CH₃ | 142°–147° dec. |
| 11 | S | —NH—C₆H₄—SO₂N₃ | 151°–154° dec. |
| 12 | S | —NHC₄H₉ | 144°–145° dec. |
| 13 | O | —NHC₄H₉ | 133°–136° dec. |
| 14 | S | —NH—C₆H₄—OCH₃ | 175°–178° dec. |
| 15 | O | —NH—C₆H₄—OCH₃ | 180°–181.5° dec. |
| 16 | S | —NH—C₆H₄—N(CH₃)₂ | 131.5°–133° dec. |
| 17 | S | —NHCH₃ | 127°–130° dec. |
| 18 | O | —NHCH₃ | 178°–181° dec. |

| No. | Aminobenzene Compound (Mole) | Acylating Agent (Mole) | Reaction Solvent | Reaction Time | Precipitating Solvent |
|---|---|---|---|---|---|
| 1 | 0.01 | 0.01 | glyme | 2 hrs. | none |
| 2 | 0.01 | 0.01 | glyme | 3 days | water |
| 3 | 0.01 | 0.01 | glyme | 18 hrs. | water |
| 4 | 0.01 | 0.01 | glyme | 1 hr. | none |
| 5 | 0.002 | 0.002 | glyme | 1 hr. | ether |
| 6 | 0.005 | 0.005 | glyme | 1¼ hrs. | none |
| 7 | 0.005 | 0.005 | glyme | 18 hrs. | ether |
| 8 | 0.01 | 0.01 | glyme | 18 hrs. | ether |
| 9 | 0.00925 | 0.00925 | glyme | 24 hrs. | water |
| 10 | 0.01 | 0.01 | glyme | 2 days | water |
| *11 | 0.01 | 0.01 | toluene | 1 hr. | none |

*heated to reflux initially

| No. | Monoacylated arylene diamine (Mole) | Phosphorylisocyanate or Isothiocyanate (Mole) | Reaction Solvent | Reaction Time | Precipitating Solvent |
|---|---|---|---|---|---|
| 12 | 0.01 | 0.01 | glyme | ½ hr. | none |
| 13 | 0.01 | 0.01 | glyme | 18 hrs. | none |
| 14 | 0.01 | 0.01 | glyme | 24 hrs. | none |
| 15 | 0.01 | 0.01 | glyme | 18 hrs. | none |
| 16 | 0.005 | 0.005 | glyme | 24 hrs. | none |
| 17 | 0.01 | 0.01 | glyme | 45 min. | none |
| 18 | 0.01 | 0.01 | glyme | 18 hrs. | none |

PROCEDURE 13

Synthesis of 1-(3-Disubstituted Phosphoryl Thioureido)-3 or 4-(3-Substituted Ureido) Benzene Compounds (A) To a suspension of meta or para nitroaniline in an appropriate solvent, e.g. benzene, toluene, etc., is added dropwise, a solution of p-toluenesulfonylisocyanate in a suitable solvent, e.g. glyme. The suspension which forms is refluxed and stirred overnight and is vacuum filtered to yield 1-nitro-3 or 4-(p-toluenesulfonylurea) benzene.

(B) Palladium on carbon 10% is added to a solution of the 1-nitro-3 or 4-(p-toluenesulfonylurea) benzene in an appropriate solvent such as methyl cellosolve and the mixture is shaken at room temperature on a hydrogenator. After the appropriate amount of hydrogen is taken up and the spent catalyst is filtered, the solution is concentrated in vacuo to yield 1-amino-3 or 4-(p-toluenesulfonylurea) benzene.

(C) To a solution of the 1-amino-3 or 4-(p-toluenesulfonylurea) benzene in an appropriate solvent such as acetone is added the disubstituted phosphoryl isothiocyanate. The solution is allowed to stand at room temperature overnight and is poured into an appropriate solvent such as ether. The residue is suspended in water and made basic with sodium hydroxide. With vigorous stirring, the basic solution is slowly made acidic with 12 N hydrochloric acid. The suspension which forms is vacuum filtered and washed with water and dried to yield the desired compound.

Table 11 represents the results of two such syntheses.

TABLE 11

$$A\begin{matrix}NH-C(=S)-NH-P(OC_2H_5)_2\\ NH-C(=O)-NH-SO_2-\text{C}_6\text{H}_4-CH_3\end{matrix}$$

| A | Melting Point | Yield |
|---|---|---|
| 3-methylphenyl | 111°–120° slow dec. | 36.6% |
| 4-methylphenyl | 155°–157° dec. | 42% |

PROCEDURE 14

Synthesis of 1-(3-diethylphosphonothioureido)-2-(3-p-toluenesulfonyltetrahydropyrimid-2-one) benzene (a) Anhydrous sodium carbonate, 34.5 g. (0.33 mole), o-chloronitrobenzene, 47.25 g. (0.3 mole), 3-amino-1-propanol, 22.5 g. (0.3 mole), and n-butanol, 120 ml., are mixed and heated under reflux with stirring for 12 hours. The butanol is removed under reduced pressure and the residue is diluted with 300 ml. of water and steam-distilled. The residual orange oil is cooled in an ice bath whereupon it solidifies. The solid is filtered and air dried overnight to yield 46.9 g. (80%) of 3-(2-nitroanilino)-propanol.

(b) The product of (a), 30 g. (0.127 mole), is added to phosphorus oxychloride over a period of 15 minutes and the mixture is heated for one hour before the excess of oxychloride is removed under reduced pressure. The residue is warmed gently with 100 ml. of water, cooled, and extracted with ether. The combined extracts are washed with aqueous sodium carbonate and dried with magnesium sulfate. The solvent is removed to afford as an orange oil, 25.5 g. of N-3-chloropropyl 2-nitroaniline.

(c) The product of (b), 25.5 g. (0.10 mole), is added to a solution of p-toluenesulfonylisocyanate, 19.7 g. (0.10 mole) is 250 ml. of dry acetonitrile. A mild exotherm results after which the mixture is heated under reflux for one hour. After cooling, the solvent is evaporated to afford a dark oil. The oil is triturated with ether and the solid which precipitates is filtered and air-dried to yield 32.2 g. (78%) of 1-nitro-2-(3-p-toluenesulfonyl-1-chloropropylureido)benzene.

(d) The product of (c), 20.6 g. (0.05 mole), is added to a stirred solution of potassium hydroxide in 70% aqueous ethanol. After refluxing for one hour, the solution is cooled and filtered. The resultant solid is air dried to yield 17.9 g. (95%) of 1-nitro-2-(3-p-toluenesulfonyltetrahydropyrimidin-2-one)-benzene, m.p. 168°–170° C. Recrystallization from 95% ethanol gives analytical crystals, m.p. 167°–170° C.

(e) The product of (d), 8 g. (0.01213 mole), and 600 mg. of 10% palladium on carbon is suspended in 250 ml. of absolute ethanol. The mixture is hydrogenated at 50 psi. for two hours. The solution is filtered, the precipitate is dissolved in chloroform and then refiltered to remove the catalyst. The filtrate is concentrated to yield 5.7 g. (78%), of 1-amino-2-(3-p-Toluenesulonyl tetrahydropyrimidin-2-one) m.p. 208–211; recrystallization from acetonitrile, m.p. 209–211.

(f) The product of (e), 3.45 g. (0.01 mole) is suspended in 50 ml. of acetonitrile to which is added, with stirring, diethoxyphosphorylthiocyanate, 1.95 g. (0.01 mole). The mixture is stirred at room temperature overnight and then concentrated under reduced pressure. The resulting oily solid is treated with 0.1 N sodium hydroxide solution and filtered. The filtrate is acidified with 3 N hydrochloric acid and the precipitated solid is filtered and air dried to yield (quantitative) the final product.

PROCEDURE 15

Synthesis of Alkali Metal Salts

The alkali metal hydroxide is added to a suspension of a compound of this invention in water, and the mixture is stirred until a solution forms. The solution is concentrated in vacuo at room temperature, and the residue dried in a vacuum oven at room temperature for 2½ days.

The sodium salt of the following compound is made according to this procedure.

$$\text{C}_6\text{H}_4\begin{matrix}NH-C(=O)-NH-SO_2-\text{C}_6\text{H}_4-CH_3\\ NH-C(=S)-NH-P(=O)(OC_2H_5)_2\end{matrix}$$

| Compound (Mole) | Sodium hydroxide (50%) (Mole) | M.P. |
|---|---|---|
| 0.01 | 0.02 | 150–153 decomp. |

PROCEDURE 16

Synthesis of Metal Salt Complexes

The dialkali metal salt of a compound of this invention is reacted with an appropriate metal salt in an aqueous medium. A precipitate forms, is filtered off, thoroughly washed and dried to give the desired product. Table 12 presents the results of eight such syntheses.

TABLE 12

Metal Salt Complexes $$\text{C}_6\text{H}_4\begin{matrix}NH-C(=S)-NHP(OC_2H_5)_2\\ NH-C(=O)-NH-SO_2-\text{C}_6\text{H}_4-CH_3\end{matrix}$$

| Metal Salt | M.P. |
|---|---|
| 1. CuCl₂ | 168°–170° dec. |
| 2. ZnCl₂ | 167°–168° dec. |
| 3. NiCl₂ | 172°–175° dec. |
| 4. CoCl₂ | 165°–167° dec. |
| 5. SnCl₂ | 126°–129° |
| 6. CdCl₂ | 149°–152° |
| 7. MnCl₂ | 158° |

$$\text{C}_6\text{H}_4\begin{matrix}NH-C(=S)-NH-P(OC_2H_5)_2\\ NH-C(=O)-NH-P(=O)(OC_2H_5)_2\end{matrix}$$

TABLE 12-continued

Metal Salt Complexes

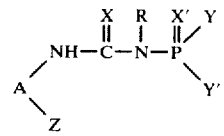

| Metal Salt | M.P. |
|---|---|
| 8. $ZnCl_2$ | 164°–165° dec. |

All of the compounds described in this application can be used as anthelmintics for combatting infections in avians, cats, dogs, sheep, porcine, bovine, equine and man. As set forth below, these compounds can be administered in liquid or preferably tablet form to the host.

The compounds of this invention may be combined advantageously with other anthelmintics. Since the prepared compounds have activity not found in certain other anthelmintics such as thiabendazole, phenothiazine, piperazine, tetramisole, pyrantel, niclosanide, bunamidine, etc. combinations of the present compounds and other anthelmintics would possess clinical utility. Appropriate dosage forms containing a plurality of anthelmintically active compounds are accordingly contemplated by the present invention.

For use against species of roundworms as well as tapeworms, the preferred compounds are most desirably administered between about 12 and 100 mg/kg; while for use against tapeworms only, the effective dose may be somewhat lower, e.g., 3 to 50 mg/kg.

A wide variety of formulations of conventional pharmaceutical excipients may be employed. By way of illustration, Examples I and II present formulations for tablets and chewable tablets, respectively,

EXAMPLE 1

A tablet of the following composition is formulated:

| | |
|---|---|
| Active Compound | 220 mg. |
| Lactose | 53.23 mg. |
| Magnesium Aluminum Silicate Gel | 2.24 mg. |
| Starch | 13.13 mg. |
| Calcium Stearate | 0.65 mg. |
| Microcrystalline Cellulose | 35.75 mg. |
| TOTAL | 325 mg. |

A granulation, containing water by the use of Magnesium Aluminum Silicate and starch in the form of pastes, is tableted to form flat level, double or quarter scored, uncoated tablets, of 6 to 9 S.C.A. hardness. The appropriate number (and fraction) of tablets is administered to the host, e.g. one tablet per 20 lbs. body weight.

EXAMPLE II

An alternative formulation is in the form of a palatable chewable tablet. Each chewable tablet contains:

| | |
|---|---|
| Active Compound | 110 mg. |
| Dried Fish Meal | 1027 mg. |
| Dried Liver Powder, Bovine | 1027 mg. |
| Soybean Oil Meal | 97 mg. |
| Cane Sugar | 239 mg. |
| TOTAL | 2500 mg. |

The present invention may be embodied in other specific forms without departure from the spirit or essential attributes thereof and, accordingly, reference should be made to the appended claims, rather than to the foregoing specification as indicating the scope of the invention.

We claim:

1. A compound of the formula:

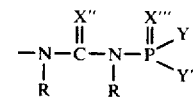

wherein A is a divalent arylene group optionally substituted with
 (a) halogen;
 (b) cyano;
 (c) nitro;
 (d) di($C_1$–$C_{18}$)alkylamino;
 (e) vicinal alkylene of from 2 to 6 carbon atoms; or
 (f) a group of the formula: $R^1(A')_a$
 wherein $R^1$ is
  1. an alkyl group of from 1 to 4 carbon atoms;
  2. a substituted or unsubstituted aromatic group containing from 6 to 10 atoms in the aromatic ring;
 A' is oxygen, sulfur, sulfinyl, sulfonyl or carbonyl; and
 a is an integer of 0 to 1;
R is
 (a) hydrogen;
 (b) ($C_1$–$C_{10}$)alkyl;
 (c) ($C_1$–$C_{10}$)haloalkyl;
 (d) ($C_3$–$C_6$)cycloalkyl;
 (e) ($C_2$–$C_{11}$)alkoxyalkyl;
 (f) ($C_1$–$C_{10}$)cyanoalkyl;
 (g) ($C_3$–$C_6$)alkenyl;
 (h) ($C_3$–$C_6$)haloalkenyl;
 (i) ($C_3$–$C_6$)alkynyl;
 (j) ($C_3$–$C_6$)haloalkynyl;
 (k) optionally substituted aralkyl of up to 11 carbon atoms; or
 (l) substituted or unsubstituted ($C_6$–$C_{10}$)aryl;
Y is R', OR', N(R')$_2$ or SR' and
Y' is OR', N(R')$_2$ or SR' wherein R' is alkyl($C_1$–$C_4$), substituted alkyl($C_1$–$C_4$), aralkyl($C_7$–$C_{10}$), alkenyl ($C_1$–$C_4$), substituted alkenyl($C_1$–$C_4$), phenyl, substituted phenyl, naphthyl or substituted naphthyl;
X is oxygen or sulfur;
X' is oxygen or sulfur; and
Z is a group of the formula:

$$-\underset{R}{N}-\underset{}{\overset{X''}{\overset{\|}{C}}}-\underset{R}{N}-\overset{X'''}{\overset{\|}{P}}\diagdown_{Y'}^{Y}$$

wherein
 R is as above defined;
 X" is oxygen or sulfur, provided that when X" is sulfur, X is oxygen;
 X'" is oxygen or sulfur; and
 Y and Y' are as above defined; or a pharmaceutically acceptable salt of said compound.

2. A compound according to claim 1 having the formula:

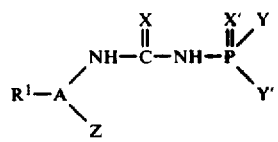

wherein

A is divalent phenylene or naphthylene;

X is oxygen or sulfur;

X' is oxygen or sulfur;

Y and Y' are independently OR', N(R')$_2$ or SR' wherein

R' is (C$_1$-C$_4$)alkyl, (C$_2$-C$_4$)alkoxyalkyl, (C$_1$-C$_4$)haloalkyl, (C$_3$-C$_4$)alkenyl, phenyl or substituted phenyl, R$^1$ is hydrogen or
 (a) (C$_1$-C$_4$)alkyl;
 (b) (C$_1$-C$_4$)alkoxy;
 (c) (C$_3$-C$_4$)alkenyl;
 (d) halogen;
 (e) nitro; or
 (f) a group of the formula:

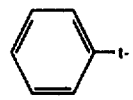

wherein t is carbonyl, sulfur, sulfinyl, or sulfonyl, provided that R$^1$ does not represent more than one

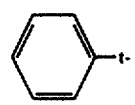

group; and represents from one to four substituents when A is phenylene and from one to six substituents when A is naphthylene; and Z is a group of the formula:

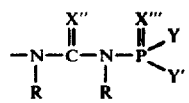

wherein R is
 (a) hydrogen;
 (b) (C$_1$-C$_{10}$)alkyl;
 (c) (C$_1$-C$_{10}$)haloalkyl;
 (d) (C$_3$-C$_6$)cycloalkyl;
 (e) (C$_2$-C$_{11}$)alkoxyalkyl;
 (f) (C$_1$-C$_{10}$)cyanoalkyl;
 (g) (C$_3$-C$_6$)alkenyl;
 (h) (C$_3$-C$_6$) haloalkenyl;
 (i) (C$_3$-C$_6$)alkynyl;
 (j) (C$_3$-C$_6$)haloalkynyl;
 (k) optionally substituted aralkyl of up to 11 carbon atoms; or
 (l) substituted or unsubstituted (C$_6$-C$_{10}$)aryl;

X'' is oxygen or sulfur, provided that when X'' is sulfur, X is oxygen;

X''' is oxygen or sulfur; and

Y and Y' are as above defined.

3. A compound according to claim 2 having the formula:

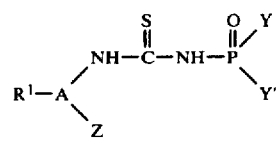

wherein

A is ortho, meta, or para phenylene, or ortho naphthylene;

Y is OR' and Y' is OR' or SR' wherein R' is
 (a) (C$_1$-C$_4$)alkyl
 (b) (C$_2$-C$_4$)alkoxyalkyl;
 (c) allyl;
 (d) (C$_1$-C$_4$)haloalkyl;
 (e) phenyl; or
 (f) phenyl substituted with (C$_1$-C$_4$)alkyl, nitro, halogen, (C$_1$-C$_4$) alkoxy, (C$_1$-C$_4$) haloalkyl, or di(C$_1$-C$_4$) alkylamino;

R$^1$ is hydrogen or (C$_1$-C$_4$)alkyl, (C$_1$-C$_4$) halogen, benzoyl, benzenesulfonyl, benzenesulfinyl, or phenylthio; and represents from one to two substituents on the ring provided that R$^1$ does not represent more than one benzoyl, benzenesulfonyl, benzenesulfinyl or phenyl thio substituent, and Z is a group of the formula:

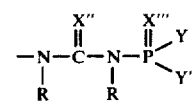

wherein R is
 (a) hydrogen;
 (b) (C$_1$-C$_{10}$)alkyl;
 (c) (C$_1$-C$_{10}$)haloalkyl;
 (d) (C$_3$-C$_6$)cycloalkyl;
 (e) (C$_2$-C$_{11}$)alkoxyalkyl;
 (f) (C$_1$-C$_{10}$)cyanoalkyl;
 (g) (C$_3$-C$_6$)alkenyl;
 (h) (C$_3$-C$_6$)haloalkenyl;
 (i) (C$_3$-C$_6$)alkynyl;
 (j) (C$_3$-C$_6$)haloalkynyl;
 (k) optionally substituted aralkyl of up to 11 carbon atoms; or
 (l) substituted or unsubstituted (C$_6$-C$_{10}$) aryl;

X'' is oxygen or sulfur, provided that when X'' is sulfur, X is oxygen;

X''' is oxygen or sulfur; and

Y and Y' are as above defined.

4. A compound according to claim 3 wherein

R' is (C$_1$-C$_4$)alkyl, (C$_2$-C$_4$)alkoxyalkyl, allyl or (C$_1$-C$_4$)haloalkyl, and R$^1$ is (C$_1$-C$_4$)alkyl, (C$_1$-C$_4$)alkoxy, halogen or benzoyl.

5. A compound according to claim 1 wherein X''' is oxygen.

6. The compound according to claim 1 having the formula:

[Structure: phenyl with NH-C(=X)-NH-P(=X')(Y)(Y') and N(R¹)-C(=X")-NH-R³]

wherein
R¹ is hydrogen;
R² is hydrogen;
R³ is $$-\overset{O}{\underset{\|}{P}}(OC_2H_5)_2$$

X is oxygen;
X' is oxygen;
X" is oxygen;
Y is —OC₂H₅ and
Y' is —OC₂H₅.

7. The compound according to claim 1 having the formula:

[Structure as above]

wherein
R¹ is hydrogen;
R² is hydrogen;
R³ is $$-\overset{O}{\underset{\|}{P}}(OC_2H_5)_2;$$

X is sulfur;
X' is oxygen;
X" is oxygen;
Y is —OC₂H₅ and
Y' is —OC₂H₅.

8. The compound according to claim 1 having the formula:

[Structure as above]

wherein
R¹ is hydrogen;
R² is hydrogen;
R³ is $$-\overset{O}{\underset{\|}{P}}(OC_2H_5)_2;$$

X is sulfur;
X' is sulfur;
X" is oxygen;
Y is —OC₂H₅ and
Y' is —OC₂H₅.

9. The compound according to claim 1 having the formula:

[Structure as above]

wherein
R¹ is hydrogen;
R² is hydrogen;
R³ is $$-\underset{OC_2H_5}{\overset{O}{\underset{\|}{P}}}\hspace{-0.5em}\diagup\hspace{-0.5em}SC_3H_7\text{-iso}\ ;$$

X is sulfur;
X' is oxygen;
X" is oxygen;
Y is —OC₂H₅ and
Y' is —OC₂H₅.

10. The compound according to claim 1 having the formula:

[Structure as above]

wherein
R¹ is hydrogen;
R² is hydrogen;
R³ is $$-\underset{OC_2H_5}{\overset{O}{\underset{\|}{P}}}\hspace{-0.5em}\diagup\hspace{-0.5em}SC_3H_7\text{-iso}\ ;$$

X is oxygen;
X' is oxygen;
X" is sulfur;
Y is —OC₂H₅ and
Y' is —OC₂H₅.

11. An anthelmintic composition for oral administration comprising an anthelmintically effective amount of the compound of claim 1 and a pharmaceutically acceptable carrier.

12. An anthelmintic composition for oral administration comprising an anthelmintically effective amount of the compound of claim 2 and a pharmaceutically acceptable carrier.

13. An anthelmintic composition for oral administration comprising an anthelmintically effective amount of the compound of claim 3 and a pharmaceutically acceptable carrier.

14. An anthelmintic composition for oral administration comprising an anthelmintically effective amount of the compound of claim 4 and a pharmaceutically acceptable carrier.

15. An anthelmintic composition for oral administration comprising an anthelmintically effective amount of the compound of claim 5 and a pharmaceutically acceptable carrier.

16. An anthelmintic composition for oral administration comprising an anthelmintically effective amount of the compound of claim 6 and a pharmaceutically acceptable carrier.

17. An anthelmintic composition for oral administration comprising an anthelmintically effective amount of the compound of claim 7 and a pharmaceutically acceptable carrier.

18. An anthelmintic composition for oral administration comprising an anthelmintically effective amount of the compound of claim 8 and a pharmaceutically acceptable carrier.

19. An anthelmintic composition for oral administration comprising an anthelmintically effective amount of the compound of claim 9 and a pharmaceutically acceptable carrier.

20. An anthelmintic composition for oral administration comprising an anthelmintically effective amount of the compound of claim 10 and a pharmaceutically acceptable carrier.

21. A composition according to claim 11 in the form of a tablet.

22. A composition according to claim 11 in the form of a flavored, chewable tablet.

23. A composition according to claim 11 in the form of a flavored liquid.

24. A method for combatting a helminth infection in a host animal which comprises administering an anthelmintically effective amount of a compound of claim 1 to said animal.

25. A method for combatting a helminth infection in a host animal which comprises administering an anthelmintically effective amount of a compound of claim 2 to said animal.

26. A method for combatting a helminth infection in a host animal which comprises administering an anthelmintically effective amount of a compound of claim 3 to said animal.

27. An method for combatting a helminth infection in a host animal which comprises administering an anthelmintically effective amount of a compound of claim 4 to said animal.

28. A method for combatting a helminth infection in a host animal which comprises administering an anthelmintically effective amount of a compound of claim 5 to said animal.

29. A method for combatting a helminth infection in a host animal which comprises administering an anthelmintically effective amount of a compound of claim 6 to said animal.

30. A method for combatting a helminth infection in a host animal which comprises administering an anthelmintically effective amount of a compound of claim 7 to said animal.

31. A method for combatting a helminth infection in a host animal which comprises administering an anthelmintically effective amount of a compound of claim 8 to said animal.

32. A method for combatting a helminth infection in a host animal which comprises administering an anthelmintically effective amount of a compound of claim 9 to said animal.

33. A method for combatting a helminth infection in a host animal which comprises administering an anthelmintically effective amount of a compound of claim 10 to said animal.

34. The method of claim 24 wherein the host animal is an avian.

35. The method of claim 24 wherein the host animal is a cat.

36. The method of claim 24 wherein the host animal is a dog.

37. The method of claim 24 wherein the host animal is a sheep.

38. The method of claim 24 wherein the host animal is a porcine.

39. The method of claim 24 wherein the host animal is a bovine.

40. The method of claim 24 wherein the host animal is an equine.

41. The method of claim 24 wherein the host animal is man.

* * * * *